US005601835A

United States Patent [19]
Sabel et al.

[11] Patent Number: 5,601,835
[45] Date of Patent: Feb. 11, 1997

[54] POLYMERIC DEVICE FOR CONTROLLED DRUG DELIVERY TO THE CNS

[75] Inventors: Bernhard A. Sabel, Egmating, Germany; Andrew Freese, Jamaica Plain, Mass.; William M. Saltzman, Baltimore, Md.; Matthew J. During, Westport, Conn.

[73] Assignee: Massachusetts Institute of Technology, Cambridge, Mass.

[21] Appl. No.: 180,117

[22] Filed: Jan. 12, 1994

Related U.S. Application Data

[63] Continuation of Ser. No. 20,190, Feb. 16, 1993, abandoned, which is a continuation of Ser. No. 795,046, Nov. 20, 1991, abandoned, which is a continuation of Ser. No. 407,930, Sep. 15, 1989, abandoned, which is a continuation-in-part of Ser. No. 43,695, Apr. 29, 1987, Pat. No. 4,883,666.

[51] Int. Cl.$^6$ .................... A61F 2/00; A61K 9/00
[52] U.S. Cl. .................... 424/424; 128/898; 128/899; 424/422; 424/423; 424/486; 424/487; 435/182
[58] Field of Search .................... 424/422–426, 424/484, 486, 487; 435/177, 180, 182; 604/890.1, 891.1; 128/898, 899

[56] References Cited

U.S. PATENT DOCUMENTS

| | | | |
|---|---|---|---|
| 3,625,214 | 12/1971 | Higuchi | 424/424 |
| 3,832,252 | 8/1974 | Higuchi | 156/86 |
| 3,880,991 | 4/1975 | Yolles | 424/432 |
| 3,948,254 | 4/1976 | Zaffaroni | 128/833 |
| 3,965,255 | 6/1976 | Block et al. | 424/450 |
| 3,976,071 | 8/1976 | Sadek | 424/425 |

(List continued on next page.)

FOREIGN PATENT DOCUMENTS

| | | |
|---|---|---|
| 0168862 | 1/1986 | European Pat. Off. . |
| 0226061 | 6/1987 | European Pat. Off. . |
| 2167662 | 6/1986 | United Kingdom . |

OTHER PUBLICATIONS

A. D. Schwope, et al. *Chemical Abstrcts* 84, 304 Abstract No. 84:184849x.
R. Willette, *Chemical Abstracts* 84(13) 304 Abstract No. 184855w (Jun. 28, 1976).
Suzuki and Price *Journal of Pharmaceutical Sciences* 74(1) 21–24 (Jan. 1985).
Cardinal, "Matrix Systems", Chapter 2, *Medical Applications of Controlled Release*, vol. 1, 41–67, 87–89 (CRC Press, Inc., Florida 1984).
Siegel, R. A., et al., *Pharm. Res.* 1, 2–10 (1984).
Boer, et al., *J. Neuroscience Methods* 11, 281–289 (Elsevier: The Netherlands, 1984).
McRae–Degueurce, et al., *Neuroscience Letters* (Ireland) 92(3), 303–309 (1988).

(List continued on next page.)

*Primary Examiner*—John C. Bleutge
*Assistant Examiner*—Robert H. Harrison
*Attorney, Agent, or Firm*—Arnall Golden & Gregory

[57] ABSTRACT

Disclosed is a polymeric drug delivery system for delivery of any substance to the central nervous system. The delivery system is preferably implanted in the central nervous system for delivery of the drug directly to the central nervous system. These implantable devices can be used, for example, to achieve continuous delivery of dopamine, which cannot pass the blood brain barrier, directly into the brain for an extended time period. The implantable devices display controlled, "zero-order" release kinetics, a life time of a minimum of several weeks or months even when the devices contain water soluble, low molecular weight compounds, biocompatibility, and relative non-invasiveness. The polymeric devices are applicable in the treatment of a variety of central nervous system disorders including Parkinson's disease, Alzheimer's dementia, Huntington's disease, epilepsy, trauma, stroke, depression and other types of neurological and psychiatric illnesses.

14 Claims, 2 Drawing Sheets

U.S. PATENT DOCUMENTS

| | | | |
|---|---|---|---|
| 4,069,307 | 1/1978 | Higuchi | 424/432 |
| 4,164,560 | 8/1979 | Folkman et al. | 424/422 |
| 4,177,256 | 12/1979 | Michaels | 424/427 |
| 4,217,898 | 8/1980 | Theeuwas | 424/433 |
| 4,263,273 | 4/1981 | Appelgren et al. | 425/451.7 |
| 4,278,087 | 7/1981 | Theeuwes | 424/405 |
| 4,346,709 | 8/1982 | Schmitt | 424/426 |
| 4,351,337 | 9/1982 | Sidman | 424/425 |
| 4,391,797 | 7/1983 | Folkman et al. | 424/425 |
| 4,675,189 | 6/1987 | Kent et al. | 424/490 |
| 4,832,686 | 5/1989 | Anderson | 424/426 |
| 4,832,957 | 5/1989 | Dempski et al. | 424/469 |
| 4,883,666 | 11/1989 | Sabel et al. | 424/422 |
| 4,913,903 | 4/1990 | Sudmann et al. | 424/426 |
| 4,952,402 | 8/1990 | Sparks et al. | 424/426 |
| 4,983,400 | 1/1991 | Dempski et al. | 514/565 |
| 5,019,372 | 5/1991 | Folkman et al. | 424/423 |
| 5,106,627 | 4/1992 | Aebischer et al. | 424/424 |
| 5,114,719 | 5/1992 | Sabel et al. | 424/422 |
| 5,156,844 | 10/1992 | Aebischer et al. | 424/424 |

U.S. PATENT DOCUMENTS

Sladek, et al, *J. Neurosurg.* 68,337–351 (1981).
Cotzias, et al, *New Eng. J. Med.* 276(7) 374–379 (Feb. 16, 1967).
Yahr, et al, *Arch. Neurol.* 21,343–354 (Oct. 1969).
Rossor, et al, *J. Neurolog. Sci.* 46,385–392 (1980).
Gonzalez, et al., *Abstracts Soc. Neuroscience* No. 353,15 (1988).
Juncos, et al, *J. Neurol. Neurosurg. Psych.* 50, 194–198 (1987).
Quinn, et al, *Lancet* 412–415 (Aug. 21, 1982).
Shoulson, *Neurol.* 25,1144–1148 (Dec. 1975).
Cedarbaum, *Neruol.* 37,1607–1612 (Oct. 1987).
Mouradian, et al, *Ann. Neurol.* 22,475–479 (1987).
Martin, *JAMA* 216(12),1979–1983 (Jun. 21, 1971).
Tolosa, et al, *Neurol.* 25,177–183 (Feb. 1975).
Nutt, *Ann. Neurol.* 22, 535–540 (Mar. 3, 1987).
Mars, *Arch. Neurol.* 28,91 (Feb. 1973).
Juncos, et al, *Arch Neurol.* 44,1010–1012 (Oct. 1987).
Bergmann, et al, *Adv. Neurol.* 45,463–467 (1986).
Brady, *Molecular Basis of Lysosomal Storage Disorders* 461–474 (Academic Press 1984).
Pincus, et al, *Arch.Neurol.* 44,1006–1009 (1987).
Saarinen, et al, *Acta Neurol. Scandinav.* 58,340–349 (1978).
Birket–Smith, et al, *Lancet* 431–432 (Feb. 24, 1973).
Cedarbaum, et al, *Neurol.* 37,233–241 (1987).
Curzon, et al, *Lancet* 781 (Apr. 7, 1973).
Woods, et al, *Lancet* 1391 (Jun. 16, 1973).
Chase, et al, *Adv. in Neurol.* 45,477–480 (1986).
Brown, L., et al., "Controlled Release of Insulin From Polymer Matrices–Control of Diabetes in Rats" *Diabetes*, vol. 35, pp. 692–697 (Jun., 1966).
Brown, L., et al., "Controlled Release of Insulin from Polymer Matrices–In Vitro Kinetics", *Diabetes*, vol. 35, No. 6, pp. 684–691 (Jun., 1966).
Hsieh, D. S., et al., "Zero–Order Controlled–Release Polymer Matrices for Micro–and Macromolecules" *Journal of Pharmaceutical Sciences*, vol. 72, No. 1, pp. 17–22 (Jan., 1983).

POLYMERIC DEVICE FOR CONTROLLED DRUG DELIVERY TO THE CNS

This is a continuation of U.S. Ser. No. 08/020,190, filed Feb. 16, 1993, now abandoned, which is a continuation of application Ser. No. 07/795,046, filed on Nov. 20, 1991, now abandoned, which is a continuation of U.S. Ser. No. 07/407,930, filed Sep. 15, 1989, now abandoned, which is a continuation-in-part application of U.S. patent Ser. No. 07/043,695 "Controlled Drug Delivery System for Treatment of Neural Disorders", filed Apr. 29, 1987, by Bernhard A. Sabel, Andrew Freese, and Mark Saltzman, now U.S. Pat. No. 4,883,666.

BACKGROUND OF THE INVENTION

Many drugs exist which pass the blood brain barrier and are therefore suitable for the treatment of certain disorders of the central nervous system. However, a number of additional substances exist which are of potential clinical usefulness, but that do not pass through the blood brain barrier. It is therefore desirable to develop methods to deliver these drugs directly to the central nervous system.

The prior art discloses several attempts to deliver drugs to the central nervous system (CNS) in a continuous fashion. The most widely known device is the ALZET™ minipump, a reservoir-type system which can continuously deliver a solution containing a drug, for example, dopamine or a dopamine agonist, for up to four weeks. Delivery is through a canula which is chronically implanted into the CNS, as described by Hargraves, et al. *Life Sci* 40, 959–966 (1987); and Yebenes, et al. *J Neural Transm* [Supp] 27, 141–160 (1988)). Implantable pumps for delivery of substances to the CNS are described by R. E. Harbaugh et al. *Neurosurgery,* 23(6), 693–698 (1988).

There are several disadvantages to this approach, including the relatively short period of time with which substances can be delivered to the CNS, the relative instability of the drug in solution, and recent reports of toxic effects of this method to deliver drugs to the CNS (H. L. Vahlsing et al., *Soc. for Neuroscience Abstracts* 14, No. 331.6 (1988). In addition, concerns over safety for reservoir-based pump systems in the case of damage or malfunction has tempered enthusiasm for this technique.

It is therefore desirable to obtain a device which is capable of delivering substances to CNS in a continuous fashion for prolonged periods of time without the need to suspend the drug in solution. Over the past twenty years, oral sustained release formulations of such drugs as aspirin have gained popularity. However, these formulations do not achieve the constant plasma (and hence brain) levels of drugs, critical for the effective treatment of neurological or psychiatric disorders.

For these reasons, it is desirable to provide a non-oral or mechanical controlled drug release system for use in treating nervous system disorders. Despite the use of controlled drug delivery systems in the treatment of a variety of diseases, including malignancy, and metabolic defects such as diabetes, it has never been directly applied to the treatment of non-malignant nervous disorders, including ischemic, metabolic, congenital or degenerative disorders, wherein the purpose is to replace lost function or prevent defective function. This is despite the fact that the technology for encapsulating bioactive compounds within a polymeric device has been known for a long time and people have suggested that such devices might be useful for treatment of nervous disorders. There are a number of reasons why this technology has not been successfully reduced to practice, including the complexity of the nervous system, the difficulties in delivery of substances to the nervous system, especially the brain, and the differences in response of individual patients to drugs delivered locally at a constant rate and dosage rather than in discrete doses via the circulatory system. An example of a prior art polyanhydride drug delivery device is taught by U.S. Pat. No. 3,625,214 to Higuchi. This device consists of a spirally wound layer of biodegradable polymer overlaid with drug which is released as the polymer degrades. Although it is noted that a variety of configurations can be used to achieve a desired release pattern, there is no teaching of how to treat neural disorders where the goal is to replace or supplement the biological function of the cells, not just to introduce a substance having a particular effect when administered by conventional means.

The nervous system is complex and physically different from the rest of the body. There are two "systems", the central nervous system and the peripheral nervous system. As used in the present invention, "central nervous system" includes both the brain and spinal cord and "peripheral nervous system" includes the nerves, ganglia, and plexus. The peripheral nervous system is divided into the autonomic and somatic nerves. The somatic nerves innervate the skeletal muscles and the autonomic nerves supply the enervation to the heart, blood vessels, glands, other visceral organs, and smooth muscles. The motor nerves to the skeletal muscles are myelinated, whereas the postganglionic autonomic nerves are generally nonmyelinated. The autonomic nervous system is further divided into the sympathetic and the parasympathetic nerves. In general, the sympathetic and parasympathetic systems are viewed as physiological antagonists. However, the activities of the two on specific structures may be different and independent or integrated and interdependent.

As is readily apparent, both the physical differences and interrelatedness of these components of the nervous system must be taken into account in designing a drug delivery system. As stated in *The Pharmacological Basis of Therapeutics*, edited by Gilman et al, on page 10 (MacMillan Publishing Company, New York 1980) "The distribution of drugs to the CNS from the blood stream is unique, mainly in that entry of drugs into the CNS extracellular space and cerebrospinal fluid is restricted.... Endothelial cells of the brain capillaries differ from their counterparts in most tissues by the absence of intercellular pores and pinocytotic vesicles. Tight junctions predominate, and aqueous bulk flow is thus severely restricted.... The drug molecules probably must traverse not only endothelial but also perivascular cell membranes before reaching neurons or other drug target cells in the CNS.... In addition, organic ions are extruded from the cerebrospinal fluid into blood at the choroid plexus by transport processes similar to those in the renal tubule. Lipid-soluble substances leave the brain by diffusion through the capillaries and the blood-choroid plexus boundary. Drugs and endogenous metabolites, regardless of lipid solubility and molecular size, also exit with bulk flow of the cerebrospinal fluid through the arachnoid villi.... The blood-brain barrier is adaptive in that exclusion of drugs and other foreign agents such as penicillin or tubocurarine protects the CNS against severely toxic effects. However, the barrier is neither absolute nor invariable. Very large doses of penicillin may produce seizures; meningeal or encephalitic inflammation increases the local permeability."

There are other problems. The immune system does not function within the CNS in the same manner as it does in the tissues and corporeal systems. A representative example of the problems in treating nervous system disorders is in the treatment of bacterial meningitis with antibiotics. Very toxic and high concentrations of the drugs are required.

During the 1980s, more sophisticated drug delivery systems were designed to achieve a truly constant, or "controlled", release of either low or high molecular weight compounds. One such drug delivery system is a polymer matrix fabricated with ethylene-vinyl acetate (EVA). This matrix consists of a continuous phase of polymer carrier with a dispersed phase of drug powder particles. A delivery device containing dry drug particles, instead of drug in solution, is advantageous since the drug remains stable in dry form for significantly longer periods of time than in solution.

The mechanism of drug release from polymer matrix has been proposed to be as follows: as soon as the polymer is brought into contact with a physiological medium such as saline, the medium has access to the outer most particles of the water-soluble phase of the polymer, i.e. the drug particles at the surface of the matrix. The diffusion of the drug particles leaves behind pores in the polymer matrix through which the medium gains access to the next layer of drug particles. In this way, drug molecules continuously diffuse out through the previously emptied pores and their interconnecting channels into the aqueous environment. A number of fabrication factors influence the kinetics of drug release: drug-particle size, drug loading, matrix coating, and drug solubility.

As first demonstrated in U.S. Ser. No. 07/043,695 filed Apr. 29, 1987, U.S. Pat. No. 4,883,666, controlled-release polymers can be used for the delivery of substances to the CNS. Other investigators have subsequently confirmed that the use of controlled release is both efficacious and advantageous over other methods for delivery of drugs to the CNS. For example, McRae-Degueurce et al., *Neuroscience Letters (Ireland)* 92(3), 303–309 (1988), disclose an implantable microencapsulated dopamine device and Gonzalez et al., *Abstracts of the Soc. Neuroscience*, No. 353.15 (1988), disclose a dopamine secreting polymeric device. Although these demonstrated delivery to the CNS, neither showed controlled (zero-order) drug delivery to the CNS, nor extended term release. A method whereby a small controlled-delivery device implanted into the CNS was used to deliver vasopressin to the cerebrospinal fluid with zero-order kinetics was described by Boer, et al., *J. Neuroscience Methods*, 11, 281–289 (Elsevier: The Netherlands 1984), but zero-order release was not obtained for a period beyond one week.

In summary, only in U.S. Ser. No. 07/043,695, U.S. Pat. No. 4,883,666 has a method been disclosed whereby substances can be delivered to the CNS which is clinically practicable and safe and which is characterized by long-term controlled release kinetics. This type of release is particularly desirable as a treatment for a variety of CNS disorders since it allows targeting drugs to the brain without adverse side effects arising from variations in delivery.

An example of a disorder of the CNS which has been especially difficult to treat is Parkinson's disease. The treatment of Parkinson's Disease patients with the dopamine biosynthetic precursor L-DOPA (in conjunction with a decarboxylase inhibitor) is an effective approach for the reduction of extrapyramidal symptoms in Parkinson's disease and has enjoyed wide acceptance. Nevertheless, a number of problems still remain unresolved which are of concern, particularly to patients in advanced states of the disease.

Treatment of patients with Parkinson's disease is primarily by systemic administration of dopamine and dopamine agonists. In the first few years of the disease, the majority of Parkinson's patients show a clinically stable response to L-DOPA therapy despite fluctuations in plasma L-DOPA levels. However, after several years of oral L-DOPA therapy, the CNS progressively fails to smooth out amplitude swings of plasma (L-DOPA) into a sustained biological response and patients start fluctuating clinically. Symptom reduction, for example in motor performance ("on"-period), alternates, sometimes abruptly, with periods where L-DOPA treatment seems ineffective and symptoms reappear ("off"-period). The emergence of such clinical fluctuations are often referred to as the "wearing-off" effect and, with further progression of the disease, they become a serious problem for the patient.

In many patients, these fluctuations in clinical response appear to be synchronized with fluctuations in plasma levels of L-DOPA associated with the timing and dose of oral ingestion of L-DOPA in conjunction with some form of dopa-decarboxylase inhibitor (e.g. Sinemet or Madopar). This observation suggests that fluctuations in plasma levels of L-DOPA may be directly responsible for the unstable clinical response. In an attempt to alleviate this problem, studies have been conducted using various methods of slow delivery of L-DOPA or dopamine receptor agonists, including i.v.-infusion, implantable or external reservoir pump systems or oral slow release preparations, such as Sinemet CR 3 - CR 5 and Madopar HBS, as well as others. Although the application of i.v.-infusion or pump systems have optimal or near-optimal release kinetics, these approaches are unsatisfactory with respect to practicality or reliability.

In contrast, oral slow-release preparations are relatively practical and reliable, but kinetic studies show that they do not provide constant ("controlled") delivery but simply temporarily retard the release ("sustained"-release). This temporary sustained release is not only due to gastric emptying, but also due to the release kinetics of the oral preparation itself. Although oral slow-release preparations do appear to improve the condition of patients in some cases, in others they are ineffective or have even been reported in rare cases to be detrimental. Taken together with earlier i.v. infusion studies, these results nevertheless provide evidence that controlled delivery of L-DOPA is a superior treatment modality.

Another type of treatment which has been attempted is by brain tissue grafting. A permanent reduction of lesion-induced behavioral deficits has been achieved in animal models of Parkinson's disease using grafts of fetal dopaminergic brain tissue or autologous adrenal medullary tissue. These animal experiments have raised the enthusiastic hope of both scientists and the public alike that permanent functional restoration by tissue grafts may also be achieved in patients. This has prompted a vigorous effort to test the efficacy of the transplantation technique in human subjects. Despite earlier preliminary reports of successful clinical trials from Sweden and Mexico, enthusiastic appraisals have given way to a more realistic view, recognizing theoretical and practical problems associated with the brain grafting approach. Included among the problems still under discussion are questions asking whether the implantation of fetal brain tissue is indeed effective in patients, and acceptable from an ethical point of view.

It is therefore an object of the present invention to provide a method and compositions for treating disorders of the CNS, for example, Parkinson's disease, which eliminate the plasma drug level swings and clinical response fluctuations after oral systemic administration.

SUMMARY OF THE INVENTION

Implantable polymeric devices which are able to provide controlled delivery of biologically active molecules into the central nervous system for an extended period of time following implantation adjacent or into the central nervous system have been developed. The polymeric devices are preferably implanted directly into the central nervous system and can be used to achieve continuous delivery of drugs such as dopamine, which cannot pass the blood brain barrier, directly into the brain for an extended time period. The implantable devices display controlled, "zero-order", release kinetics, a life time of a minimum of several weeks or months even when the devices contain water soluble, low molecular weight compounds such as L-dopa, biocompatibility, and relative non-invasiveness. The drug is preferably dispersed in solid form within the polymer, avoiding problems with instability and loss of activity when in solution. The polymeric devices are applicable in the treatment of a variety of central nervous system disorders including Parkinson's disease, Alzheimer's dementia, Huntington's disease, depression and other types of neurological and psychiatric illnesses.

BRIEF DESCRIPTION OF THE DRAWINGS

FIG. 3, lower panel, shows the intrastriatal dopamine levels measured by microdialysis. Dopamine concentration in polymer implanted rats (filled circles) were significantly elevated compared to controls (open circles) and maintained for a period of at least 65 days.

DETAILED DESCRIPTION OF THE INVENTION

Figure 1:
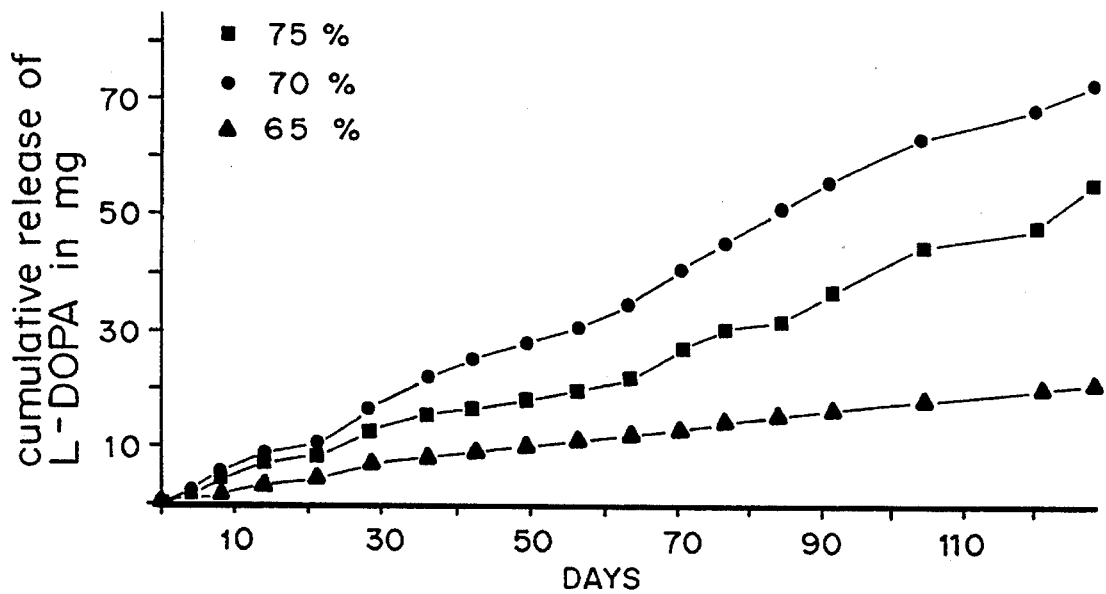
FIG. 1 is a graph of the cumulative in vitro release of L-Dopa from EVA devices having one opening, comparing release from devices containing 65%, 70% or 75% L-Dopa.

There are a variety of compounds having an effect on nervous system disorders which can be incorporated into polymers for sustained release into the CNS. Examples include neurohumoral agents, neurotransmitters such as acetylcholine, compounds which modify the quantity or activity of the neurotransmitters, and antagonists and agonists of these neurotransmitters. A variety of disorders can be treated by implantation of polymeric devices containing dispersed biologically active molecules into or adjacent the central nervous system. The advantage of implantation directly within the brain is that it provides a mechanism for delivery of molecules which do not pass through the blood brain barrier, as well as delivery of molecules in lower total quantities with less loss of activity as a result of passage through the body or storage or delivery via an implantable pump, particularly of compounds that are unstable in solution.

The polymeric devices are preferably formed by dispersion of the drug within liquified polymer, as described in U.S. Ser. No. 07/043,695, filed Apr. 29, 1987, U.S. Pat. No. 4,883,666, the teachings of which are incorporated herein. The device is a matrix-system. The term "matrix" as used herein is defined as a polymeric carrier matrix that is biocompatible and sufficiently resistant to chemical and/or physical destruction by the environment of use such that the matrix remains essentially intact throughout the release period. The polymer matrices should be biocompatible, plastically deformable, have limited water sorptivity, and be to a limited extent permeable to the passage of small, aqueous-soluble molecules. The term "aqueous" as used herein includes biological fluids, saline and physiological buffer solutions.

Polymeric materials suitable for forming the matrix include the naturally occurring and commercially available polymers, such as acyl substituted cellulose acetates and alkyl derivatives thereof; partially and completely hydrolyzed alkylene-vinyl acetate copolymers, unplasticized polyvinyl chloride, crosslinked homo- and copolymers of polyvinyl acetate, crosslinked polyesters of acrylic and methacrylate; polyvinyl alkyl ethers; polyvinyl fluoride, silicone; polycarbonate, polyurethane; polyamide, polysulphones; styrene acrylonitrile copolymers, crosslinked poly(ethylene oxide); poly(alkylenes); poly(vinyl imidazole); poly(esters); poly(ethylene terephthalate); and chlorosulphonated polyolefines.

In the preferred embodiment, the polymeric material used for forming the matrix is the ethylene-vinyl acetate copolymer (EVA) commercially available from Dupont (Elvax 40W). Techniques for preparation of these copolymers are disclosed in U.S. Pat. Nos. 2,200,429; 2,398,785; and 2,947,735, in British Patent Nos. 589,927 and 582,093, and in *Crystalline Olefin Polymers*, edited by Raff, R. A. V., and Doak, V. W., Part II, pages 261 to 266, (Interscience Publishers Inc., New York 1964).

The delivery device is a two-phase system which is manufactured using standard techniques such as blending, mixing or the equivalent thereof, following selection of the biologically active material to be delivered and an appropriate polymer for formation of the matrix. The general method of solvent casting as disclosed by Siegel and Langer, "Controlled release of polypeptides and other macromolecules", *Pharmaceutical Research* 1, 2–10 (1984), is modified so that drug is dispersed within the devices to create channels and pores to the surface for release of the drug at the desired rate. Where appropriate, a coating impermeable to the drug is placed over a portion of the drug containing polymer matrix to further regulate the rate of release. Using the method described by the prior art results in polymer samples with undesirable release kinetics. Scanning electron microscopic visualization of the polymer section loaded with L-DOPA revealed that polymers fabricated with the prior art methods displayed pores and channels even before the matrix had released any drug, indicating that fluid could gain access to all layers of the polymeric device is a short period of time, with resulting rapid and non-linear diffusion of the drug into the environment.

In order to obtain preferred release kinetics, the prior art method was altered to prevent channel and pore formation, thus reducing the accessibility of the fluids to the loaded core of the polymer and extending the period in which release of the drug takes place. The alterations of the fabrication method considered desirable included the following steps: 1. reduction of relative solvent quantity used for mixing the drug with the polymer (EVA), 2. substantially eliminating freeze-drying, and 3. application of vacuum during the entire evaporation phase. The amount of solvent was reduced since rapidly evaporating solvent might contribute to pore-formation. This was a particular concern when the polymer was then dried by freezing (−20° C). As a result, the polymer crystallization induced by freezing was only limited to the step where the glass mold was charged with liquid matrix containing dispersed drug particles and lasted for only a few minutes. Alternatively, the evaporation phase was performed at room temperature in order to reduce pore formation in the core of the polymer. Pore formation occurs more readily when the slab remains at −20° C. for several days, as is standard in the prior art. It is also advantageous to conduct the evaporation step under vacuum at room temperature to provide further significant reductions in pore formation. The result of these modifications are polymer matrices that contain very few channels and pores.

The composition formed by the method described above consists of a two-phase system having an interpenetrating phase of an agglomerate of a plurality of clusters of molecules that form at higher loading of the polymer a network of substantially contiguous particles in the polymeric matrix phase.

The present invention is further understood with reference to the following non-limiting examples of the fabrication, implantation, and release kinetics of a controlled drug delivery device for release of compounds to the CNS. Although specific to release of dopamine and L-dopa for treatment of Parkinson's disease, the method and compositions are equally applicable to other neurological disorders or depression. Examples are Alzheimer's Disease and Huntington's Chorea. In Alzheimer's dementia, the predominant pathology is a depletion in the levels of the transmitter acetylcholine. An animal model of Huntington's Disease was recently used to assess the effects of fetal cholinergic brain transplants. Both of these diseases are likely to prove to be treatable with artificial implants which slowly release transmitters or transmitter agonists or antagonists. Essentially any transmitter, its precursor, its agonist or its antagonists can be entrapped into the appropriate polymer using methods known to those skilled in the art, formed into the appropriate shape and implanted in an area targeted to alleviate symptoms.

Intracerebral implants containing substances that would otherwise not pass the blood brain barrier have potential use as therapies for hitherto untreatable disorders. For example, intracerebral implants containing large molecular weight molecules, such as many of the proteins, may be useful for treating metabolic disorders for which no effective therapy exists as yet. One such case is a class of disorders collectively referred to as "lysosomal storage diseases" and includes the inherited Tay Sachs or Gaucher's diseases. In such diseases, the brain lacks certain functional enzymes which are needed for the breakdown of otherwise toxic levels of compounds such as gangliosides and cerebrosides. Treatment of enzyme deficiencies in man with injections of enzymes, isolated from human or animal sources, outside of the nervous system is normally associated with a host of problems. In addition to the immunological reaction which can both destroy the administered enzyme and harm the patient, there is the possibility of undesirable enzyme action on substrates in areas other than those in need of therapy. Furthermore, enzymes are prone to premature inactivation in non-target extracellular and intracellular regions before reaching the blood brain barrier which they then cannot pass. A controlled release of such enzymes from polymer brain implants offers a unique opportunity to specifically target the enzyme into the affected areas of the brain, diminishing levels of toxic accumulated metabolites and restoring normal neuronal function.

Another important application of the polymeric drug delivery devices of the present invention is in the treatment of depression. Depression strikes one out of every ten Americans at one point in their life. It is usually treated with antidepressants such as tricyclics and MAO inhibitors, in conjunction with psychotherapy. The phasic nature of conventional administration of these drugs presents a number of problems. In addition, patient compliance by severely depressed patients is a particularly troublesome problem. Polymer implants containing antidepressants would eliminate these and other problems of existing therapies. In schizophrenia, which is treated with antipsychotics, patient compliance is so poor that the patient must often be hospitalized merely to administer the drug. The polymeric implants also address this disorder and may reduce the likelihood of toxic side-effects due to long term, high dosage therapy, such as tardive dyskinesia. There are a variety of potential applications of slow-release technology to neuroscience research. One of these applications is in tissue culture work. A major problem of in vitro research is the fact that the substrates for transmitters are-used up or inactivated over time. Many studies, such as those investigating biochemical and physiological responses to long term exposure to neuromodulatory agents, are limited by the absence of at continuous, consistent and inexpensive method of delivering compounds. One application is in the use of tissue cultures in the neuroscience area. A polymeric device could be placed into a tissue culture dish for release of one or several of a variety of compounds, such as neurotransmitters, growth factors, and chemotactic agents. These research applications could have similar use in alleviating the problems in the industrial scale production of pharmaceuticals or chemicals by large mammalian cell fermenters which often require constant levels of growth factors.

There are also a variety of in vivo research applications of slow release technology for the neurosciences. Included among these are the investigation of behavioral and physiological effects of one or several transmitter(s) released slowly into a specific brain area.

The release of neuroactive compounds from hydrophobic ethylene-vinyl acetate copolymer (EVA) matrices according to the present invention has been demonstrated in vitro and in an animal model. Long term, linear release of both low molecular weight and neurally active substances, L-dopa, dopamine and GM1 gangliosides, has been achieved.

EXAMPLE 1

Kinetics of in Vitro Release of Dopamine and L-DOPA

Polymer fabrication

The fabrication of L-DOPA containing polymers was a modification of a method described in U.S. Ser. No. 07/043, 695. Briefly, ethylene-vinyl acetate (EVA) was washed, and slabs containing 65% to 75% L-DOPA (Sigma St. Louis, Mo.) by weight were formed by solvent casting. Rectangular pieces (15×30×2 mm) were cut out of the slab and subsequently coated by additional layers of ethylene-vinyl acetate copolymer. The coating was done in such a way that the loaded polymer matrix was either surrounded completely by a non-permeable barrier, or such that it had one opening to allow access of medium to the loaded core. This coating was achieved by impaling the matrix on a 30 gauge needle surrounded by a hollow steel tube (2 mm diameter), followed by immersion into liquid nitrogen for about 10 sec, then coating in a 20% (w/v) EVA/solvent solution. Following the evaporation of the solvent, the removal of the needle and steel pin resulted in a 2 mm opening in the otherwise impermeable barrier.

Kinetics of L-DOPA release from polymer in vitro

Quadruplicates of the L-DOPA containing polymer were individually immersed in glass vials containing 20 ml of 150 mM NaCl, 0.2% EDTA solution (as antioxidant) and then incubated at 37° C. on an oscillating platform. Every time L-DOPA release was monitored by spectrophotometric analysis (at 280 nm), the bathing solution was replaced. The release rate was calculated by comparison with spectrophotometric evaluation of known standards and identity of the compound was confirmed at various time points using High Performance Liquid chromatography (HPLC).

As shown in FIG. 1, L-DOPA release was virtually linear for a period of at least 130 days, at which time this study was terminated. The loading of the polymer with L-DOPA had no apparent influence on the order of the release kinetics, although the absolute amount released was greater with increasing loading. Polymeric devices with only 30% loading did not show appreciable release, suggesting that the proposed release mechanism (diffusion through communicating channels and pores) is correct, since loading at this concentration apparently did not permit sufficient development of pores and interconnected channels. The higher the loading of the polymer with drug particles, the more pores and interconnecting channels are formed, resulting in greatly increased absolute quantities of release, which cannot be explained simply by the greater total quantity of drug in the polymer.

Kinetics of Dopamine release in vitro

Figure 2:
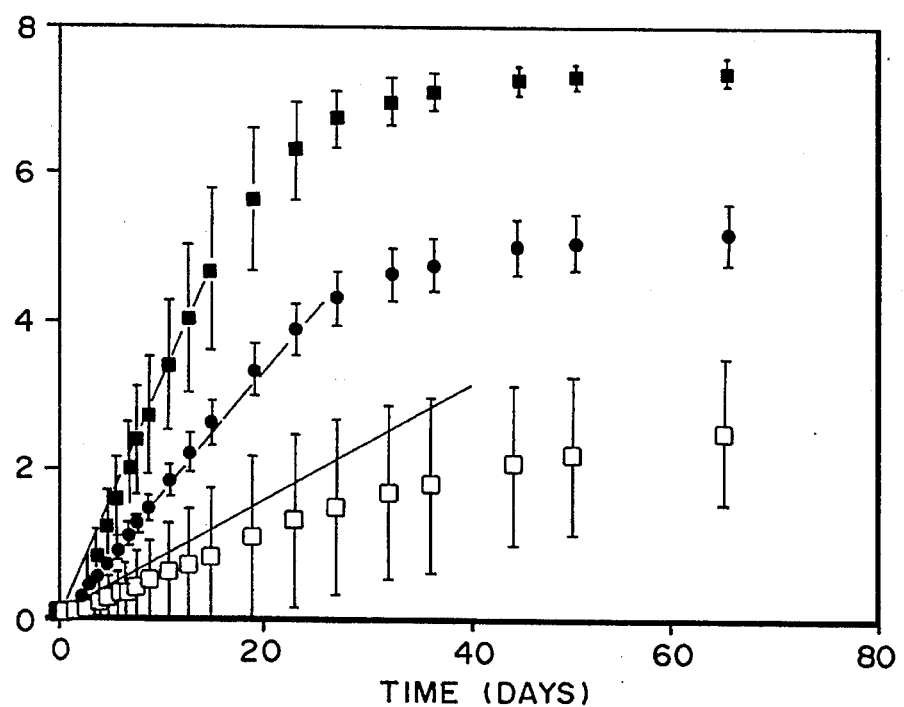
FIG. 2 is a graph of the cumulative in vitro release of dopamine from EVA devices having one opening, comparing release from smaller devices than compared in FIG. 1, containing 30% (open squares), 40% (filled circle) or 50% (filled square) dopamine.

The methodology for the fabrication of dopamine-containing polymers for controlled release of dopamine in the central nervous system is similar to that described above. However, because the these devices were used to deliver L-Dopa directly into the CNS where dopamine can act directly, polymers were fabricated which were substantially smaller (discs with 4 mm diameter 1 mm thick) and which had a lower loading of 30% 40% or 50%. Quadruplicates of loaded matrix were again surrounded by an impermeable coat, and a small pinhole opening was created in the coat as described above. FIG. 2 shows the cumulative release of dopamine from such matrix samples where only one opening was present in the otherwise impermeable barrier. In contrast to the L-DOPA polymers, matrices with a 50% loading did not display linear release of dopamine but an asymptotic release curve was observed. With decreased loading, linearity of release improved; matrices with 30% loading showed virtual linear release of dopamine for a period of at least 65 days, at which time the study was terminated.

EXAMPLE 2

In Vivo Release of Dopamine and Effect on Behavior

The successful design of a polymer matrix which is capable of releasing dopamine at a constant rate for a prolonged period of time provides a potential therapeutic alternative to intracerebral grafting of fetal mesencephalic or adult medullary tissue. By permitting localized delivery of dopamine to the striatum from a polymeric implant, it might be possible to restore deficient dopamine levels in patients with Parkinson's Disease. The in vivo release of dopamine into the striatum of rats, using intracerebral dialysis, was therefore determined.

In vivo release of dopamine from EVA pellets implanted in rats was demonstrated as follows. In the first example, intracerebral dialysis was used to monitor extracellular levels of dopamine in the striatum of pentobarbitone anaesthetized rats. In the second example, behavior was correlated with release of dopamine from implanted EVA pellets.

The Neurological Implantation of Dopamine Containing Ethylene-Vinyl Acetate Pellets into the Brains of Male Sprague-Dawley Rats: ECF Dopamine Levels Surgery and dialysis assay Under general anesthesia, male Sprague-Dawley rats (180–220 g) received an intracerebral implant of a dopamine containing polymer (30% loading, one opening), which was placed according to standardized stereotaxic coordinates: the dimensions of the polymer implants were about 4 mm in diameter and 1 mm in depth, and they were placed adjacent to the striatum in an appropriate cavity created in the neocortex by mild aspiration. The center of the cavity was 0.4 mm anterior to bregma and 2.6 mm lateral to the midline suture. Either a control (n=4) or a dopamine-containing polymer (n=12) was implanted with the opening facing the dorsal surface of the striatum. Dopamine and its major metabolites dihydroxyphenylacetic acid (DOPAC) and homovanillic acid (HVA) were measured by in vivo dialysis at various time points up to 65 days following implantation. For this purpose, a dialysis probe (Carnegie Medicin, Solna, Sweden, 4 mm membrane length, 0.5 mm outer diameter) was implanted into the striatum (AP: +2.1 mm relative to bregma; L: 1.9 mm; DV: −7.0 mm). Probes were perfused with an artificial cerebrospinal fluid (flow rate of 1.5 µl of 0.5M perchloric acid. Dialysis samples were assayed immediately thereafter by a highly sensitive reverse-phase, isocratic HPLC system with coulometric detection. After an initial 90-min period of "injury-release", stable dopamine levels were recorded for at least four fifteen minute periods.

Figure 3A:
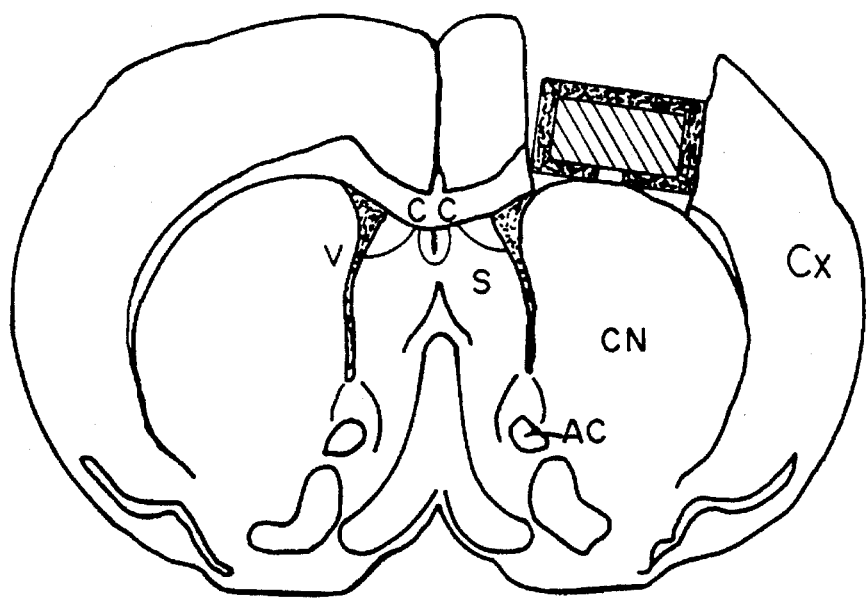
FIG. 3, upper panel, is a cross-sectional view of a coronal section through the rat brain at the level of the striatum, showing the cavity in neocortex (Cx) and the polymer containing dopamine. The opening through which the dopamine diffuses into the environment is faced down towards the dorsal surface of the caudate nucleus (CN).
Figure 3B:
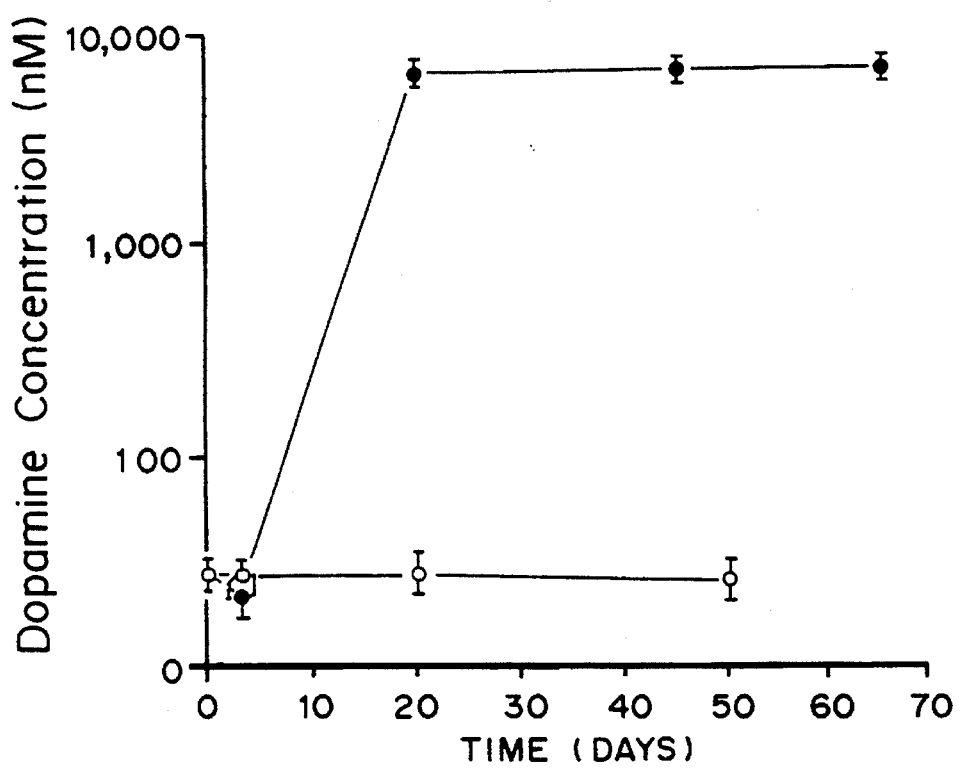

As FIG. 3(lower panel) shows, extracellular dopamine concentrations reached up to 7.2 µM at post-implantation days 10 through 65, a significant elevation over the control values of about 26 nM. Starting with post-implantation day 20, the extracellular dopamine concentration was stable until at least day 65 (at which point the experiment was terminated). Furthermore, dialysis measurements takenon day 45 revealed no appreciable dopamine extracellular fluid concentration fluctuations during the course of 7 hrs.

ECF concentrations of this order have not been previously reported even with treatments such as amphetamine nor high potassium in a perfusate and ischaemia which cause massive release of dopamine. There is no doubt therefore that these results reflect a major release of dopamine into the extracellular fluid of the implanted striatum, that such release is not evident on the third day, but is seen by the twentieth day and persists for at least two months.

Histology

After termination of the dialysis experiments, the rats were perfused with 4% paraformaldehyde in 0.1M sodium phosphate buffer. After cutting the brains coronally at 40 µm intervals on a microtome, the sections were stained with neutral red for Nissl substance and evaluated for gross morphology using light microscopy. With the exception of a small zone of gliosis at the surface of the striatum, the implantation device did not appear to have resulted in abnormal striatal gross morphology.

The Neurosurgical Implantation of Dopamine Containing Ethylene-Vinyl Acetate Pellets into the Brains of Male Sprague-Dawley Rats: Behavioral Correlation Three 350 g male Sprague-Dawley rates were anesthetized by i.p. injection of 50 mg nembutal/kg and 0.1 cc atropine. The fur was then shaved from their heads and each rat placed in a Kopf sterotaxic device. Using an Emesco Drill and an American Optical scope, the skull was carefully removed in a 205 mm×5 mm square centered 1.5 mm anterior to the bregma and 3 mm lateral to the midline suture on either side. Cortex was carefully suctioned out, as well as corpus callosum, until the surface of the striatum could be seen. Then, in a blind manner, the surgeon implanted pellets into each side of the brain.

The first rat had a coated pellet containing 20% dopamine implanted on the right side, and an EVA pellet control, containing no other substances, implanted on the left. The second rat had the dopamine pellet implanted on the left side and the control pellet implanted on the right. The third animal had three 4 mm×0.5 mm×0.5 mm strips of uncoated dopamine-containing (20%) EVA implanted within the corpus striatum in the left hemisphere, and a control pellet on the right side.

After recovery from surgery, the animals were placed in a rotometer which can measure the number of turns in each of two directions (clockwise or to the right; counterclockwise or to the left). The ratio of turns to the right and turns to the left are reported and indicative of rotation in a preferred direction. The results are presented in Table II. The implantation of the ethylene vinyl acetate polymer containing dopamine induces rotation to the contralateral (opposite) side when implanted on one side of the brain, in or above the corpus striatum, which is the expected behavior due to an increase in dopamine release. TABLE II:Rotometer Values of Dopamine-EVA Polymer Implanted Rats (Right:Left)

| Time: | zero h | 10 h | 16 h | 32 h |
|---|---|---|---|---|
| Rat 1 | 0:0 | 62:265 | 91:370 | 205:490 |
| Rat 2 | 0:0 | 28:0 | 52:4 | 243:90 |
| Rat 3 | 0:0 | 48:106 | 1940:148 | 4860:252 |

In summary, the evidence shows that both L-DOPA and dopamine can be released in a controlled, "zero-order" release for prolonged periods of time (at least 65 days for dopamine and 130 days for L-DOPA). Two practical applications of this technology to the treatment of Parkinson's patients are therefore: (a) the peripheral implantation of L-DOPA polymers or (b) the implantation of dopamine polymers directly into the central nervous system. L-DOPA containing polymers could be implanted subcutaneously into patients with Parkinson's Disease. Based on the studies above, both the rate and the lifetime of the peripheral implants are adequate for clinical applications.

The foremost advantage of this approach is the possibility that the controlled delivery of L-DOPA in conjunction with decarboxylase inhibitor will eliminate the enormous fluctuations of plasma L-DOPA levels and their clinical correlates. It is conceivable that the patient population that would benefit from polymer implants are not only those in the later stages of the disease (those suffering from "on-off" or "wearing-off" syndromes), but also those earlier in the progression of the disease. Implantation at early stages of the disorder might, by virtue of keeping the dose constant and at a minimum, even retard or preclude the appearance of the "on-off" and "end-of-dose" responses typically found at the more advanced stages of the disease.

Further, since i.v. infusion requires substantially lower L-DOPA doses than oral delivery, it is possible that lower doses may also be useful when delivered using peripheral polymer implants, in sharp contrast to the finding that oral sustained-release preparations require more L-DOPA than conventional tablets.

Because of a potential service life-time of several months, this treatment modality would also be more convenient for the patient and could eliminate some of the compliance problems seen with oral ingestion. In addition, because gastrointestinal (G1) absorption could be avoided, less drug would be wasted and side effects could be minimized. Finally, the polymer can be implanted during a relatively non-invasive ambulatory surgery and, unlike internal or external reservoir pumps, the possibility of excess drug release after mechanical failure or breakage of the device is negligible.

Potential disadvantages of the EVA polymer matrix is that it must be replaced after linear release has ceased and that no short-term dose adjustments can be made, unless the implant is supplemented with oral low-dose formulations. However, biodegradable polymer implants could be used which would not require removal. A number of biodegradable polymers are approved for use by the Food and Drug Administration, including polyanhydrides, polylactic acid and polyglycolic acid, and copolymers thereof. By imbedding small magnets within the polymer matrix, an additional level of control can be achieved by applying an external magnetic field.

Because the absolute amounts of dopamine needed for delivery into the brain are very small, it is expected that a dopamine containing polymer implant of appropriate size could release sufficient quantities of the compound for at least one year, and possibly several years.

Modifications and variations of the method and compositions for linear release of compounds to the CNS will be obvious to those skilled in the art from the foregoing detailed description of the invention. Such modifications and variations are intended to come within the scope of the appended claims.

We claim:

1. A method for treating disorders characterized by insufficient function of the central nervous system comprising:

selecting a compound for treating the disorder by replacing or supplementing a normal function in the central nervous system selected from the group consisting of L-dopa, dopamine, carbidopa, choline, acetylcholine, cholinergic neuronotrophic agents, gangliosides, nerve growth enhancing agents, antipsychotic agents, antidepressants, excitatory amino acid antagonists and agonists, antiepileptic medications, enzymes, beta-interferon and combinations thereof;

encapsulating said compound within said polymer to form a polymeric device, the device formed of a biocompatible polymer that is plastically deformable selected from the group consisting of ethylene vinyl acetate, polyurethanes, polystyrenes, polyamide, polyacrylamide, and combinations thereof having a non-porous polymer coating thereon with one or more openings, with limited water sorptivity and slight permeability to the passage of small, aqueous-soluble molecules, wherein said compound is linearly released from said polymeric device over a sustained period of time of at least 65 days at a predetermined level and rate when implanted in a patient at a specific site within the central nervous system where the compound is released directly into the central nervous system and the device remains essentially intact throughout the release period.

2. The method of claim 1 further comprising implanting said polymeric device in a patient.

3. The method of claim 1 wherein the polymer is selected to control the rate of release of said compound.

4. The method of claim 1 further comprising forming said polymer around said compound in a thickness and with a specific area calculated to provide sustained, linear release over a predetermined period of time.

5. The method of claim 1 for alleviating the symptoms of Parkinson's disease wherein said compound is selected from the group consisting of L-dopa, carbidopa, and dopamine.

6. The method of claim 1 for treating nervous system injury wherein said compound is gangliosides.

7. The method of claim 1 for alleviating the symptoms of Alzheimer's Disease wherein said compound is a cholinergic agonist, antagonist or neuronotrophic agent.

8. The method of claim 1 for treating multiple sclerosis wherein said compound is beta-interferon.

9. The method of claim 1 for alleviating the symptoms of Huntington's Disease wherein said compound is an antagonist of excitatory amino acids.

10. The method of claim 1 wherein said encapsulated compound is implanted within the nervous tissue of the brain.

11. The method of claim 1 wherein said encapsulated compound is implanted within the spinal cord.

12. A composition for treating disorders of the central nervous system characterized by insufficient function comprising:

a compound for treating the disorder by replacing or supplementing a normal function in the central nervous system selected from the group of L-dopa, dopamine, carbidopa, choline, acetylcholine, cholinergic neuronotrophic agents, gangliosides, nerve growth enhancing agents, antipsychotic agents, antidepressants, excitatory amino acid antagonists and agonists, antiepileptic medications, and enzymes and combinations thereof;

a biocompatible non-biodegradable polymer that is plastically deformable selected from the group of polymers consisting of ethylene vinyl acetate, polyurethanes, polystyrenes, polyamide, polyacrylamide, and combinations thereof;

wherein said compound is encapsulated within said polymer to form a polymeric device having a non-porous polymer coating thereon with one or more openings, the device having limited water sorptivity, being slightly permeable to the passage of small, aqueous-soluble molecules, said polymeric device of a form to linearly released said compound over a sustained period of time of at least 65 days at a predetermined level and rate when implanted in a patient at a specific site within the central nervous system where the compound is released directly into the central nervous system and the device remains essentially intact throughout the release period.

13. The composition of claim 12 wherein the polymer composition determines the rate of release of said compound.

14. The composition of claim 12 wherein said polymer is formed around said compound in a thickness and with a specific area calculated to provide sustained, linear release over a predetermined period of time.

* * * * *

UNITED STATES PATENT AND TRADEMARK OFFICE
CERTIFICATE OF CORRECTION

PATENT NO.   : 5,601,835                                           Page 1 of 1
DATED        : February 11, 1997
INVENTOR(S)  : Bernhard A. Sabel, Andrew Freese, William M. Saltzman and Matthew J. During It is certified that error appears in the above-identified patent and that said Letters Patent is hereby corrected as shown below:

Column 1,
Line 14, insert the following:
-- STATEMENT REGARDING FEDERALLY SPONSORED RESEARCH OR DEVELOPMENT
  This invention was made with government support under grant Number NIH-2R01-GM26698 awarded by the National Institutes of Health. The government has certain rights in the invention. --

Signed and Sealed this

Eleventh Day of February, 2003

JAMES E. ROGAN
*Director of the United States Patent and Trademark Office*